United States Patent [19]

Eisenhart et al.

[11] Patent Number: 5,480,720
[45] Date of Patent: Jan. 2, 1996

[54] ADHESIVE COMPOSITION

[75] Inventors: Eric K. Eisenhart, Doylestown; Louis C. Graziano, Warrington; Jose P. Lalas, Harleysville, all of Pa.

[73] Assignee: Rohm and Haas Company, Philadelphia, Pa.

[21] Appl. No.: 204,929

[22] Filed: Mar. 1, 1994

[51] Int. Cl.$^6$ ........................................ B32B 27/38
[52] U.S. Cl. ...................... 428/414; 156/330; 156/332; 428/511; 428/520; 523/413; 523/414
[58] Field of Search .................................. 523/413, 414; 428/511, 520; 156/330, 332

[56] References Cited

U.S. PATENT DOCUMENTS

| | | | |
|---|---|---|---|
| 4,240,938 | 12/1980 | Kraft et al. | 525/419 |
| 5,037,700 | 8/1991 | Davis | 428/414 |
| 5,037,700 | 8/1991 | Davis . | |

*Primary Examiner*—Melvyn I. Marquis
*Assistant Examiner*—D. Aylward
*Attorney, Agent, or Firm*—Kevin E. McVeigh

[57] ABSTRACT

An adhesive composition includes from about 30 weight percent to about 70 weight percent solids dispersed in an aqueous medium. The solids include from about 60 weight percent to about 97.9 weight percent of a polymer having a glass transition temperature of about −40° C. to about 10° C. and including first repeating units derived from an alkyl (meth)acrylate monomer, a vinyl ester monomer, a styrenic monomer or a mixture thereof and second repeating units derived from a hydroxyalkyl (meth)acrylate monomer, a monoethylenically unsaturated nitrogenous monomer or a mixture thereof; from about 2 weight percent to about 30 weight percent of a polyfunctional epoxy resin including two or more epoxide groups per molecule; from about 0.1 weight percent to about 10 weight percent of a polyfunctional curing agent including two or more amino groups or amido groups per molecule; and from about 0.01 weight percent to about 30 weight percent of a metal salt. A method for making a laminate includes applying a layer of the aqueous adhesive composition to a first substrate layer and covering the layer of adhesive composition with a second substrate layer to form the laminated article. A laminate includes two substrate layers bonded together by an interposed layer of the solids of the adhesive composition.

24 Claims, No Drawings

ADHESIVE COMPOSITION

TECHNICAL FIELD

The present invention is directed to adhesive compositions useful for making flexible laminates and, more particularly, to aqueous adhesive compositions that are particularly well-adapted for lamination of polyolefin films.

BACKGROUND

Flexible film laminates wherein films of dissimilar polymeric materials are bonded together by an interposed adhesive layer to form a composite material are known and widely used in applications having performance criteria that cannot be met using a single film of either of the polymeric materials alone. For example, a polyester film may be bonded to a polyolefin film to provide a high-strength heat-sealable packaging material.

The adhesive layer of such laminates must develop a strong bond with each of the polymeric films of the laminate in order to resist delaminating stresses which may be directly imposed by the conditions of the end-use application and which may also arise from the dissimilar responses of the respective layers of the laminate to those conditions.

Furthermore, from the standpoint of providing an economically feasible and environmentally responsible method for manufacturing such flexible laminate materials, it is important that the adhesive layer cures rapidly at room temperature and does not require the use of volatile organic solvents.

U.S. Pat. No. 5,037,700 discloses a process for preparing a flexible laminate. The process involves the use of a room temperature curable adhesive that consists essentially of a copolymer emulsion of an alkyl (meth)acrylate, styrene or a vinyl ester and from 1 weight percent to 10 weight percent of an ethylenically unsaturated carboxylic acid in combination with an epoxy resin emulsion and a polyfunctional amine.

While the process disclosed in the U.S. Pat. No. '700 patent is said to provide a laminate characterized by superior bond strength, superior resistance to temperature extremes and superior resistance to chemicals and water, those skilled in the art will recognize that such claims are relative and that there remains an acute interest in laminates that exhibit properties superior even to those exhibited by those laminates made by the process of the U.S. Pat. No. '700 patent.

SUMMARY OF THE INVENTION

An aqueous adhesive composition is disclosed. The adhesive composition provides rapid room temperature cure with very rapid development of bond strength, high ultimate bond strength and excellent moisture resistance.

In a first embodiment, the adhesive composition includes from about 30 weight percent to about 70 weight percent solids dispersed in an aqueous medium and the solids include from about 60 weight percent to about 97.9 weight percent of a polymer having a glass transition temperature of about −40° C. to about 10° C. and including first repeating units derived from an alkyl (meth)acrylate monomer, a vinyl ester monomer, a styrenic monomer or a mixture thereof, second repeating units derived from a hydroxyalkyl (meth)acrylate monomer, a monoethylenically unsaturated nitrogenous monomer or a mixture thereof; from about 2 weight percent to about 30 weight percent of a polyfunctional epoxy resin, said polyfunctional epoxy resin including two or more epoxide groups per molecule; from about 0.1 weight percent to about 10 weight percent of a polyfunctional curing agent, said polyfunctional curing agent including two or more functional groups, each selected from the group consisting of amino groups and amido groups, per molecule and from about 0.01 weight percent to about 30 weight percent of a metal salt.

In a second embodiment, the adhesive composition includes from about 30 weight percent to about 70 weight percent solids dispersed in an aqueous medium and the solids include from about 60 weight percent to about 97.9 weight percent of a polymer having a glass transition temperature of about −40° C. to about 10° C. and consisting essentially of first repeating units derived from an alkyl (meth)acrylate monomer, a vinyl ester monomer, a styrenic monomer or a mixture thereof, second repeating units derived from a hydroxyalkyl (meth)acrylate monomer, a monoethylenically unsaturated nitrogenous monomer or a mixture thereof; said polymer including no more than 1.0 weight percent acid repeating units, said acid repeating units having at least one acid functional group per acid repeating unit; from about 2 weight percent to about 30 weight percent of a polyfunctional epoxy resin, said polyfunctional epoxy resin including two or more epoxide groups per molecule; and from about 0.1 weight percent to about 10 weight percent of a polyfunctional curing agent, said polyfunctional curing agent including two or more functional groups, each selected from the group consisting of amino groups and amido groups, per molecule.

A laminate is disclosed. The laminate includes a first substrate layer, a second substrate layer and an adhesive layer interposed between the first and second substrate layers and bonding the first and second substrate layers together. In a first embodiment of the laminate, the adhesive layer comprises the solids portion of the above-disclosed first embodiment of the aqueous adhesive composition and in a second embodiment of the laminate, the adhesive layer comprises the solids portion of the above-disclosed second embodiment of the aqueous adhesive composition.

A method for making a laminate wherein two substrate layers are bonded together by a dried layer of adhesive composition is disclosed. The method includes, in a first embodiment, applying a layer of the above-disclosed first embodiment of the aqueous adhesive composition to a first substrate layer and covering the layer of adhesive composition with a second substrate layer to form the laminate and in a second embodiment, applying a layer of the above-disclosed second embodiment of the aqueous adhesive composition to a first substrate layer and covering the layer of adhesive composition with a second substrate layer to form the laminate.

DETAILED DESCRIPTION OF THE INVENTION

The aqueous adhesive composition of the present invention includes a polymer that includes first repeating units derived from an alkyl (meth)acrylate monomer, a vinyl ester monomer, a styrenic monomer or a mixture thereof and second repeating units derived from a hydroxyalkyl (meth)acrylate monomer, a monoethylenically unsaturated nitrogenous monomer or a mixture thereof and that has a glass transition temperature (Tg) of from about −40° C. to about 10° C. Unless otherwise noted, the Tg values disclosed herein are based on measured values obtained, preferably, by differential scanning calorimetry. The terminology "(meth- )acrylate" refers collectively to acrylate and methacrylate compounds.

Suitable alkyl (meth)acrylate monomers include $(C_1–C_{20})$alkyl (meth)acrylate monomers. As used herein the terminology "$(C_1–C_{20})$alkyl" denotes an alkyl substituent group having from 1 to 20 carbon atoms per group. Suitable $(C_1–C_{20})$alkyl (meth)acrylate monomers include, for example, ethyl acrylate, butyl acrylate, 2-ethylhexyl acrylate, lauryl acrylate, cetyl acrylate, stearyl acrylate, eicosyl acrylate, methyl methacrylate, ethyl methacrylate, butyl methacrylate, isodecyl methacrylate, lauryl methacrylate, cetyl methacrylate, stearyl methacrylate, eicosyl methacrylate and mixtures thereof.

Suitable vinyl ester monomers include, for example, vinyl acetate, vinyl propionate, vinyl neononanoate, vinyl neodecanoate, vinyl-2-ethylhexanoate, vinyl pivalate, vinyl versatate or a mixture thereof.

The terminology "styrenic monomer" means polymerizable vinyl-aromatic compounds having a single unsaturated site per molecule such as, for example, styrene, alkyl-substituted styrenes such as alpha-methyl styrene, beta-methyl styrene alpha-ethyl styrene, and vinyl xylene, halogenated styrenes such as chlorostyrene, bromostyrene and dichlorostyrene, other styrene derivatives having one or more nonreactive substituent groups on the benzene nucleus as well as mixtures thereof. Styrene, alkyl-substituted styrenes such as alphamethyl styrene, beta-methyl styrene, alpha-ethyl styrene and vinyl xylene are preferred styrenic monomers.

Suitable hydroxyalkyl monomers include hydroxy$(C_1–C_8)$alkyl (meth)acrylate monomers, wherein the terminology "hydroxy$(C_1–C_8)$alkyl" denotes a hydroxyalkyl substituent group having from 1 to 8 carbon atoms per group. Suitable hydroxy$(C_1–C_8)$alkyl (meth)acrylate monomers include, for example, hydroxyethyl acrylate, hydroxyethyl methacrylate, hydroxybutyl acrylate, hydroxypropyl acrylate, hydroxypropyl methacrylate, 1-methyl-2-hydroxyethyl methacrylate and mixtures thereof.

The terminology "monoethylenically unsaturated nitrogenous monomer" includes polymerizable monoethylenically unsaturated compounds having one or more nitrogen containing functional groups per molecule, such as, for example, (mono-alkyl)amino alkyl (meth)acrylates, (di-alkyl)amino alkyl (meth)acrylates, (meth)acrylamides, alkyl (meth)acrylamides, (mono-alkyl)amino alkyl (meth)acrylamides, (di-alkyl)amino alkyl (meth)acrylamides and vinyl-substituted nitrogen-containing heterocyclic compounds. The terminology "monoethylenically unsaturated" means having a single site of ethylenic unsaturation per molecule and the terminology "(meth)acrylamide" refers collectively to acrylamide and methacrylamide compounds. Suitable ethylenically unsaturated nitrogenous monomers include, for example, N,N-dimethylamino ethyl acrylate, N,N-diethylamino ethyl acrylate, N,N-dimethylamino ethyl methacrylate, N,N-diethylamino ethyl methacrylate, N-t-butylamino ethyl acrylate, acrylamide, methacrylamide, N,N-dimethylamino propyl acrylamide, N,N-dimethylamino propyl methacrylamide, 2-vinyl pyridine and mixtures thereof.

In one embodiment, the polymer includes repeating units derived from a monoethylenically unsaturated carboxylic acid monomer. Suitable monoethylenically unsaturated carboxylic acid monomers include, for example, acrylic acid, methacrylic acid, itaconic acid, crotonoic acid, aconitic acid, atropic acid, maleic acid, fumaric acid, vinyl benzoic acid, half-esters of ethylenically unsaturated dicarboxylic acids, half-amides of ethylenically unsaturated dicarboxylic acids and mixtures thereof. Acrylic acid, methacrylic acid and mixtures thereof are preferred as the monoethylenically unsaturated carboxylic acid monomer.

The polymer may, optionally, be pre-crosslinked, that is, crosslinked during synthesis of the copolymer, by including a small amount, for example, about 0.01 weight percent (wt %) to about 5 wt %, of a polyethylenically unsaturated monomer in the monomer mixture, wherein the terminology "polyethylenically unsaturated" means having two or more sites of ethylenic unsaturation per molecule. Suitable polyethylenically unsaturated monomers include, for example, allyl (meth)acrylate, diallyl phthalate, 1,4-butylene glycol di(meth)acrylate, trimethylolpropane tri(meth)acrylate, divinyl ketone, N,N'-methylenediacrylimide, the polyallyl and polyvinyl ethers of pentaerythritol and mixtures thereof.

The polymer is made by polymerizing a monomer or a mixture of monomers and the product polymer is a random chain made of repeating units derived from the monomer or the respective monomers of the mixture. The identity and relative amounts of the monomers of the mixture are selected, within the above disclosed limits, according to methods known in the art so that the polymer produced by polymerizing the monomer mixture exhibits a $T_g$ in the above-disclosed range.

The $T_g$ of a proposed polymer composition may be estimated by methods known in the art. Once the proposed polymer composition is made, the $T_g$ of the proposed polymer composition may be measured and, optionally, the proposed composition may subsequently be refined based on comparison of the respective estimated $T_g$ and the measured $T_g$ values.

In a preferred embodiment, the polymer is made in the form of an aqueous emulsion of polymeric particles by a free radical-initiated aqueous emulsion polymerization reaction. Suitable emulsion polymerization techniques are well known in the art.

We have found that synthesis of the above disclosed polymer by aqueous emulsion polymerization results in a polymeric product having more acid repeating units than can be accounted for by the relative amount of any acid monomer charged to the polymerization reactor and that, even in reactions wherein no acid monomer is charged, the polymeric product includes a small amount of acid repeating units. The additional acid units are present in an amount up to about 1.0 wt % and more typically, in an amount from about 0.1 wt to about 0.3 wt %. While not wishing to be bound by theory, it is believed that "extra" acid units are generated during the polymerization as the result of hydrolysis of a small number of the substituent groups of the monomeric reactants and of the growing polymer. As used herein the terminology "acid repeating unit" means a repeating unit of the polymer that has a measurable, for example, by titration or by nuclear magnetic resonance spectroscopy, acid functional group, regardless of the manner in which the acid functional group was derived, and includes both those acid repeating units derived from the above disclosed monoethylenically unsaturated carboxylic acid monomers and those additional acid-functional repeating units believed to have been generated by hydrolysis. All acid repeating unit weight percentages disclosed herein are calculated as if the acid units were derived from acrylic acid.

In a preferred embodiment, the polymer of the aqueous polymer emulsion is in the form of particles of about 50 nanometers to about 4000 nanometers in diameter.

In a preferred embodiment, the polymer includes greater than 80 wt %, more preferably from about 85 wt % to about 95 wt %, first repeating units and from about 0.1 wt % to about 20 wt %, more preferably from about 5 wt % to about 15 wt %, second repeating units.

In a preferred embodiment, the polymer includes from 0 wt % to about 10 wt % third repeating units derived from a monoethylenically unsaturated carboxylic acid.

Preferably, the first repeating units of the polymer are derived from an alkyl (meth)acrylate monomer, a vinyl ester monomer or a mixture thereof.

Preferably, the second repeating units of the polymer are derived from a hydroxyalkyl (meth)acrylate monomer.

In a first "low acid" embodiment, the polymer includes first repeating units, second repeating units and no more than 1.0 wt %, preferably less than or equal to about 0.8 wt %, acid repeating units.

In a second low acid embodiment, the polymer includes first repeating units, second repeating units and from 0 wt % to less than or equal to about 0.5 wt % repeating units derived from a monoethylenically unsaturated carboxylic acid monomer.

In a third low acid embodiment, the polymer consists essentially of from about 85 wt % to about 95 wt % repeating units derived from an alkyl (meth)acrylate monomer, a vinyl ester monomer, a styrenic monomer or a mixture thereof and from about 5 wt % to about 15 wt % repeating units derived from a hydroxyalkyl (meth)acrylate monomer, a monoethylenically unsaturated nitrogenous monomer or a mixture thereof.

In a "high acid" embodiment, the polymer includes first repeating units, second repeating and from greater than 1.0 wt % to about 11 wt % acid repeating units.

In a second "high acid" embodiment, the polymer includes from about 85 wt % to about 95 wt % first repeating units and from about 10 wt % to about 14 wt % second repeating units and from greater than about 0.5 wt % to about 10 wt %, preferably from greater than about 0.5 wt % to about 3 wt %, repeating units derived from a monoethylenically unsaturated carboxylic acid monomer.

In a first embodiment of the adhesive composition of the present invention, the adhesive composition includes from about 30 wt % to about 70 wt %, preferably from about 45 wt % to about 60 wt %, solids dispersed in an aqueous medium and the solids include from about 60 wt % to about 97.9 wt %, more preferably from about 80 wt % to about 94.5 wt %, of an embodiment of the above-disclosed polymer, from about 2 wt % to about 30 wt %, more preferably from about 5 wt % to about 20 wt %, of an epoxy resin, from about 0.1 wt % to about 10 wt %, more preferably from about 0.5 wt % to about 5 wt %, of a curing agent and from about 0.01 wt % to about 30 wt %, more preferably from about 0.05 wt % to about 25 wt %, of a metal salt.

Suitable metal salts may be any compound that provides a source of mono-valent or poly-valent metal cations. Suitable metal cations include, for example, $K^+$, $Cs^+$, $Na^+$, $Mg^{2+}$, $Zn^{2+}$, and $Ca^{2+}$. Suitable counterions, that is, metal salt anions, include inorganic anions such as, for example, halide and hydroxide anions, and organic anions, such as, for example, acetate anions, formate artions.

In a preferred embodiment, the metal cation is selected from the group consisting essentially of $K^+$, $Cs^+$, $Mg^{2+}$ and $Ca^{2+}$. Most preferably, the metal cation is $K^+$.

The epoxy resin may be any water-dispersible compound that includes two or more epoxide functional groups per molecule. Suitable epoxy resins are commercially available and include for example, reaction products of bisphenol A or bisphenol F and epichlorohydrin, epoxidized novolac resins and reaction products of epichlorohydrin and an aliphatic polyol, such as, for example, glycerol, 1,4-butanediol, or poly(oxypropylene), and resins obtained by epoxidation with peracetic acid. The epoxy resin may be dispersed in water and then added to the aqueous emulsion of the polymer or, alternatively, may be added to the polymer emulsion as 100% epoxy resin solids and then dispersed in the aqueous medium of the polymer emulsion.

The curing agent for the epoxy resin may be any compound having two or more active hydrogen atoms per molecule. Suitable curing agents include, for example, compounds having two or more amino or amido groups per molecule such as, for example, polyamines, poly(oxypropylene) amines and polyamidoamines. Suitable polyamines include both aliphatic polyamines such as, for example, ethylene diamine, diethylene triamine, triethylene tetramine, propylene diamine, tetraethylene pentamine, butylene diamine, hexamethylene diamine and aromatic polyamines such as, for example, 1,6-diaminobenzene. Preferably, the curing agent is an aliphatic amine. Water soluble curing agents may be directly added to the aqueous emulsion of the polymer. Water-insoluble curing agents may be dispersed in water and then added to the polymer emulsion or, alternatively, may be added to the polymer emulsion as 100% curing agent solids and then dispersed in the aqueous medium of the polymer emulsion.

Preferably, the first embodiment of the adhesive composition includes from about 25% to about 125%, more preferably from about 75% to about 120%, of the stoichiometric amount of curing agent based on the total amount of epoxide groups of the epoxy resin of the adhesive composition.

Preferably, the polymer of the first embodiment of the adhesive composition of the present invention is the above-disclosed first low acid embodiment of the polymer, i.e., wherein the polymer includes no more than 1.0 wt % acid repeating units, and the adhesive composition includes from about 0.01 equivalent to about 2 equivalents metal salt per equivalent acid repeating units.

Alternatively, the polymer of the first embodiment adhesive composition of the present invention is the above-disclosed "high acid" embodiment, that is, an embodiment wherein the polymer includes from greater than 1.0 wt % to about 11 wt % acid repeating units and the adhesive composition includes from about 0.01 equivalent to about 2 equivalents metal salt per equivalent acid repeating units.

A second embodiment of the adhesive composition of the present invention includes from about 30 wt % to about 70 wt %, preferably from about 45 wt % to about 60 wt %, solids dispersed in an aqueous medium and the solids consist essentially of from about 60 wt % to about 97.9 wt %, preferably from about 80 wt % to about 94.5 wt %, of the above-disclosed first low acid embodiment of the polymer, i.e., wherein the polymer includes no more than 1.0 wt % acid repeating units, and further includes from about 2 wt % to about 30 wt %, preferably from about 5 wt % to about 20 wt %, of an epoxy resin and from about 0.1 wt % to about 10 wt %, preferably from about 0.5 wt % to about 5 wt %, of a curing agent for the epoxy resin.

The above-disclosed epoxy resin and curing agent are suitable as the respective epoxy resin and curing agent of the second embodiment of the adhesive composition.

More preferably, the polymer of the second embodiment of the adhesive is the above-disclosed second low acid embodiment of polymer wherein the polymer includes from 0 wt % to less than or equal to about 0.5 wt % repeating units derived from a monoethylenically unsaturated carboxylic acid monomer.

Most preferably, the polymer of the second embodiment of the adhesive is the third low acid embodiment of the polymer wherein the polymer consists essentially of the above-disclosed first and second repeating units, i.e., wherein none of the repeating units of the polymer are derived from a monoethylenically unsaturated carboxylic acid monomer.

In a preferred embodiment, the adhesive composition of the present invention further includes from about 0.1 part by weight (pbw) to about 30 pbw of a water soluble hydroxy-functional polymer per 100 pbw polymer. Suitable water soluble hydroxy-functional polymers include, for example, poly(vinyl alcohol), hydroxyethyl cellulose, starches and dextrins, and are commercially available.

The adhesive composition of the present invention may, optionally, further include other additives known in the art such as, for example, emulsifiers, tackifiers, solvents, pigments, fillers, curing agents, thickeners, humectants, wetting agents, biocides, adhesion promoters, colorants, waxes, antioxidants, other polymers such as, for example, polyurethane resins, neoprene rubbers, polyisoprene rubbers, polyvinylidene chloride, styrene butadiene resins, and mixtures thereof.

In a preferred embodiment, the adhesive composition of the present invention is made by adding any components of the adhesive composition other than the polymer to an aqueous emulsion of the polymer and agitating the combination to form a substantially uniform adhesive composition.

It will be appreciated by those knowledgeable in the art that the epoxy resin and curing agent components of the adhesive composition must be kept separate from each other until just prior to use of the adhesive composition. The adhesive composition may be stored as a two component system, wherein a first component of the adhesive composition includes the curing agent and a second component of the adhesive composition includes the epoxy resin and wherein the two components are combined to form the adhesive composition just prior to use of the adhesive composition. In a preferred embodiment, the adhesive composition of the present invention is made and stored as two components, wherein the first component of the adhesive composition is formed by combining the amine with the polymer emulsion and the second component of the adhesive composition includes the epoxy resin.

In a preferred embodiment, the adhesive composition of the present invention has a viscosity of from about 10 cP to about 5,000 cP, and, more preferably, of from about 10 cP to about 1,000 cP.

The adhesive composition of the present invention is useful for bonding substrates together. The adhesive composition of the present invention is particularly useful in application wherein a plurality of substrate layers are bonded together to form a laminate.

In the method of the present invention a layer of the adhesive composition is applied to a first substrate layer and the adhesive layer is covered with a second substrate layer to form a laminated article wherein the two substrate layers are bonded together by the adhesive layer. In a preferred embodiment, the substrate layers are sheet-like substrate materials.

The adhesive composition of the present invention may be applied to a surface of a substrate to be bonded by known techniques such as, for example, roll coating, wire-wound rod coating, knife coating, gravure printing and curtain coating.

Suitable substrates include, for example, paper products such as polymer films, papers, paperboards, wood, metal foils and composite substrates, that is, substrates consisting of a combination of dissimilar substrate materials such as, for example, metallized polymer films, polymer-coated paperboards and bonded wood products such as, for example, particle board.

In a preferred embodiment of the method, the adhesive layer is allowed to dry after application to the first substrate and prior to being covered with the second substrate layer.

In applications wherein at least one of a pair of substrate layers to be bonded is a porous material, the laminate may, optionally, be made by wet lamination wherein a wet adhesive layer is covered with the second substrate and is subsequently allowed to dry. Porous substrate materials are those that allow rapid transport of moisture through the material and include, for example, cardboard, wood and paper.

In applications wherein both of a pair of substrate layers to be bonded are nonporous, the adhesive layer is allowed to dry after application to the first substrate and prior to being covered with the second substrate layer. Nonporous substrate materials are those that do not allow rapid transport of moisture through the material and include, for example, metal foils, polymer films.

In a preferred embodiment of the laminate of the present invention, at least one of the substrates is a polymer film. Suitable polymer films include, for example, polyolefin films, polyester films, polyimide films, polyamide films, poly(vinyl chloride) films.

In a highly preferred embodiment of the laminate of the present invention, at least one of the substrate layers is a polyolefin film, a polyamide film or a polyester film.

In a highly advantageous embodiment, at least one of the substrate layers is selected from the group consisting of polyethylene films, polypropylene films and poly(ethyleneterephthalate) films.

In a highly preferred embodiment of the laminate of the present invention, both of the substrates are polymer films.

EXAMPLES 1–4

The aqueous polymer emulsion of Example 1 was made according to the method set forth below:

A stirred reactor containing 255.1 grams (g) of deionized (DI) water was heated to 85° C. under nitrogen. Then 11.1 g of a seed latex (45% solids, 110 nanometer (nm) diameter) and a solution of 1.3 g of ammonium persulfate in 5 g of DI water were added to the kettle. After two minutes, a feed of a monomer mixture consisting of: 201.3 g of DI water, 4.3 g of a 23.0% solution of dodecylbenzene sulfonate (DS-4, Rhone-Poulenc), 365 g of butyl acrylate, 82.5 g of methyl methacrylate, 50.0 g of hydroxyethyl acrylate, and 2.5 g of methacrylic acid, was started. At the same time as the monomer mixture feed, the following solution was fed: 0.8 g of ammonium persulfate dissolved in 49.3 g of DI water. Both the monomer mixture and the ammonium persulfate were fed for 120 min. At the completion of the monomer mixture feed, an additional 10 g of DI water was added as a rinse. The reaction was cooled, and solids adjusted to 45% by the addition of water. The final polymer had a solids content of 44.9% and a viscosity of less than 10 cPs (RVT viscometer, #3 spindle, 10 rpm).

The aqueous polymer emulsions of Examples 2–4 were made by the method disclosed above in regard to the polymer emulsion of Example 1, except that different relative amounts of the respective monomers were used. The relative composition of each the respective polymers of the polymer emulsions of Examples 1–4, expressed in terms of the weight percents (wt %) of the monomers used to make the polymers, that is, butyl acrylate (BA), methyl methacrylate (MMA), hydroxyethyl acrylate (HEA) and methacrylic acid (MAA), is set forth below in Table 1.

TABLE 1

| Example | BA (wt %) | MMA (wt %) | HEA (wt %) | MAA (wt %) |
|---|---|---|---|---|
| 1 | 73 | 16.5 | 10 | 0.5 |
| 2 | 73 | 14 | 10 | 3 |
| 3 | 73 | 17 | 10 | 2 |
| 4 | 73 | 17 | 10 | 0 |

The adhesive compositions of Examples 1A–4A were based on the respective polymer emulsions of Examples 1–4. Each of the adhesive compositions included 100 pbw polymer emulsion, 15 pbw of a 55 wt % aqueous dispersion of an epoxy resin (Daubond DC9010W55, Daubert Chemical Co.) and 1.2 pbw polyfunctional amine (tetraethylenepentamine). The adhesive compositions of Examples 1A–4A were tested according to the following procedure:

An adhesive was applied to a first substrate (a 0.00075 inch thick film of poly(ethyleneterephthalate)) using a #4 wire wound rod and dried at 200° F. for 2 minutes to provide an adhesive coated substrate having a dry adhesive coating weight of about 1.5 pounds per 3000 square feet coated substrate area (pounds per ream). The adhesive coated substrate was bonded to a second substrate (a 0.0012 inch thick film of low density poly(ethylene)) using a hot nip calendar roll and a nip temperature of 140° F. to form a laminate. The polymer films were used as received, that is, without any treatment of the surfaces of the respective films prior to lamination.

Bond strength was measured by peeling apart the layers of one inch wide strips of the laminate on a tensile testing apparatus (Instron) at a peel rate of 12 inches per minute.

Initial bond strength was measured within 30 minutes of calendaring.

The bond strength of the laminate was also measured using laminate strips maintained at room temperature for 24 hours.

Humidity resistance was characterized by maintaining one inch wide strips of laminate that had been allowed to cure under ambient conditions for 24 hours in a humidity chamber at room temperature and 100% relative humidity for 24 hours and measuring the bond strength of the laminate immediately upon removal of the laminate from the humidity chamber.

Except as otherwise, bond strength values are reported herein as Initial Bond Strength, 24 Hour Bond Strength and Bond Strength, 100% RH, each expressed in units of grams per inch of peel (g/in), the notation "ST" is used to indicate substrate failure and the notation "delaminated" is used to indicate bond failure in the absence of an applied peel stress.

The results of the testing of the compositions of Examples 1A–4A are set forth below in Table 2.

TABLE 2

| Example No. | Initial Bond Strength (g/in) | 24 Hour Bond Strength (g/in) | Bond Strength, 100% RH (g/in) |
|---|---|---|---|
| 1A | 260 | 680 | 403 |
| 2A | 260 | 340 | delamination |
| 3A | 205 | 255 | delamination |
| 4A | 290 | 500 | 390 |

The results set forth in Table 2 indicate that an adhesive composition of the present invention consisting of a low acid polymer (a polymer including less than or equal to about 0.5 wt % repeating units derived from a monoethylenically unsaturated carboxylic acid monomer), provides superior performance, in terms of initial bond strength, ultimate bond strength and humidity resistance, compared to high acid polymer (a polymer including greater than 0.5 wt % repeating units derived from a monoethylenically unsaturated carboxylic acid monomer.

COMPARATIVE EXAMPLE C2

The adhesive compositions of Comparative Example C2 was formed by adding a metal salt (potassium hydroxide) of the polymer emulsion of Example 2 in a relative amount of 1 equivalent metal salt per equivalent methacrylic acid-derived repeating units of the polymer.

The compositions of Example 2 and Comparative Example C2 were tested according to the method set forth above in Examples 1A–4A.

The results of the testing of the compositions of Example 2 and Comparative Example C2 are set forth below in Table 3.

TABLE 3

| Example No. | Initial Bond Strength (g/in) | 24 Hour Bond Strength (g/in) | Bond Strength, 100% RH (g/in) |
|---|---|---|---|
| 2 | 290 | 380 | 45 |
| C2 | 135 | 200 | delamination |

The results set forth in Table 3 indicate that addition of a metal compound (KOH) has a detrimental effect on the properties of an adhesive composition that consists of an acrylic polymer emulsion.

EXAMPLES 1B–4B AND COMPARATIVE EXAMPLES C1B–C4B

The adhesive compositions of Examples 1B–4B and Comparative Examples C1B–C4B were based on the polymer emulsions of Examples 1–4. Each of the adhesive compositions included 100 pbw polymer emulsion, 15 pbw of a 55 wt % aqueous dispersion of an epoxy resin (Daubond DC9010W55), 1.2 pbw tetraethylenepentamine.

Samples 1B–3B and Comparative Examples C1B–C3B also included 1 equivalent of a base (potassium hydroxide or ammonium hydroxide) per equivalent methacrylic acid-derived repeating units in the polymer of the emulsion.

The same relative amount of the potassium hydroxide or of ammonium hydroxide was added to the compositions of Example 4B and Comparative Example C4B (each containing 0 wt % acid monomer), respectively, as had been added to the compositions of Example 1B and C1B, that is, the compositions of Example 4B and Comparative Example C4B were each treated as if they contained 0.5 wt % methacrylic acid-derived repeating units.

The polymer emulsion (Emulsion Example No.) and the base, that is, potassium hydroxide (KOH) or ammonium hydroxide (NH$_4$OH), used and the pH of each of the compositions of Examples 1B–4B and C1B–C4B are set forth below in Table 4.

TABLE 4

| Example No. | Emulsion Example No. | Base | pH |
|---|---|---|---|
| 1B | 1 | KOH | 10.4 |
| 2B | 2 | KOH | 10.3 |
| 3B | 3 | KOH | 10.4 |
| 4B | 4 | KOH | 10.6 |
| C1B | 1 | NH$_4$OH | 10.4 |
| C2B | 2 | NH$_4$OH | 10.3 |
| C3B | 3 | NH$_4$OH | 10.5 |
| C4B | 4 | NH$_4$OH | 10.4 |

The adhesive compositions of Examples 1B–4B and Comparative Examples C1B–C4B were tested according to the procedure set forth above in regard to Examples 1A–4A.

The results of the testing of Examples 1B–4B and Comparative Examples C1B–C4B are set forth below in Table 5.

TABLE 5

| Example No. | Initial Bond Strength (g/in) | 24 Hour Bond Strength (g/in) | Bond Strength, 100% RH (g/in) |
|---|---|---|---|
| 1B | 408 | ST | ST |
| 2B | 290 | 544 | 308 |
| 3B | 280 | 545 | 255 |
| 4B | 450 | 685 | 422 |
| C1B | 260 | 680 | 403 |
| C2B | 260 | 340 | delamination |
| C3B | 205 | 255 | delamination |
| C4B | 260 | 500 | 390 |

The results set forth in Table 5 indicate that the adhesive composition of the present invention, that is, a composition that includes an acrylic polymer emulsion in combination with an epoxy resin and a curing agent for the epoxy resin and a metal salt (KOH), provides improved performance, in terms of initial bond strength, ultimate bond strength and humidity resistance, compared to an analogous composition wherein a non-metallic base (NH$_4$OH) was substituted for the metal salt.

EXAMPLES 1C–1E, 2C–2E AND 3C–3E

The adhesive compositions of Examples 1C–1E, 2C–2E and 3C–3E were based on the polymer emulsions of Examples 1–3. Each of the adhesive compositions included 100 pbw polymer emulsion, 15 pbw of a 55 wt % aqueous dispersion of an epoxy resin (Daubond DC9010W55), 1.2 pbw tetraethylenepentamine and 1 equivalent of a metal salt (either cesium hydroxide, sodium hydroxide or lithium hydroxide) per equivalent ethylenically unsaturated carboxylic acid-derived repeating units of the emulsion polymer.

The respective polymer emulsion (Emulsion Example No.) and metal salt, that is, (cesium hydroxide (CsOH), sodium hydroxide (NaOH) or lithium hydroxide (LiOH)), used in each of the compositions of Examples 1B–1E, 2B–2E and 3B–3E are summarized below in Table 6.

TABLE 6

| Example No. | Emulsion Example No. | Base |
|---|---|---|
| 1B | 1 | KOH |
| 1C | 1 | CsOH |
| 1D | 1 | NaOH |
| 1E | 1 | LiOH |
| 2B | 2 | KOH |
| 2C | 2 | CsOH |
| 2D | 2 | NaOH |
| 2E | 2 | LiOH |
| 3B | 3 | KOH |
| 3C | 3 | CsOH |
| 3D | 3 | NaOH |
| 3E | 3 | LiOH |

The adhesive compositions of Examples 1B–1E, 2B–2E and 3B–3E and Comparative Examples C1B, C2B and C3B were tested according to the methods set forth above for Examples 1A–4A.

The results of the testing of the compositions of Examples 1A–1D, 2A–2D and 3A–3D and Comparative Examples C1B, C2B and C3B are set forth below in Table 7.

TABLE 7

| Example No. | Initial Bond Strength (g/in) | 24 Hour Bond Strength (g/in) | Bond Strength, 100% RH (g/in) |
|---|---|---|---|
| 1 | 210 | 820 | 400 |
| 1C | 170 | 860 | 185 |
| 1D | 115 | 500 | 23 |
| 1E | 170 | ST | 95 |
| C1B | 170 | 500 | 270 |
| 2B | 230 | 770 | 205 |
| 2C | 200 | 680 | 32 |
| 2D | 180 | 340 | 22 |
| 2E | 180 | 340 | 22 |
| C2B | 160 | 370 | delamination |
| 3B | 270 | ST | 195 |
| 3C | 195 | 680 | 95 |
| 3D | 195 | 725 | delamination |
| 3E | 190 | 295 | delamination |
| C3B | 180 | 455 | 36 |

The results set forth in Table 7 indicate that metal compounds other than KOH also impart improved performance to the adhesive composition of the present invention.

EXAMPLES 5–7

The polymers of Examples 5–7 were made by the process set forth above in Examples 1–4, except that a small amount of potassium hydroxide was added to the monomer mixture. The composition of the polymer of Example 5 was identical to that of Example 4. The composition of polymer of Example 6 was the same as those of Examples 4 and 5, except that in Example 6 an equal relative amount (by weight) of hydroxyethyl methacrylate (HEMA) was substituted for the hydroxyethyl acrylate used in Examples 4 and 5. The composition of the polymer of Example 7 was identical to that of Example 1.

The relative amount of acid repeating units in each of the polymers of Examples 5–7 was determined by titration, according to the following method. The polymer was diluted with a 0.5 normal (N) aqueous potassium chloride solution and raised to a pH of 11 with a 0.5N potassium hydroxide solution. The polymer was then titrated to a pH of 2.5 using 0.5N hydrochloric acid. The equivalents of acid in the polymer was determined from the concentration of the titrant, the observed breaks in the titration curve and the amount of polymer titrated.

The relative composition of each of the polymers of Examples 5–7, expressed in terms of weight percent (wt %), and the relative amount of acid repeating units, expressed in terms of weight percent based on the molecular weight of acrylic acid (wt % as AA) are set forth in Table 8.

TABLE 8

| Example # | BA (wt %) | MMA (wt %) | HEA (wt %) | HEMA (wt %) | MAA (wt %) | Acid (wt % as AA) |
|---|---|---|---|---|---|---|
| 5 | 73 | 17 | 10 | 0 | 0 | 0.27 |
| 6 | 73 | 17 | 0 | 10 | 0 | 0.17 |
| 7 | 73 | 16.5 | 10 | 0 | 0.5 | 0.74 |

EXAMPLES 5A–7A

The adhesive compositions of Examples 5A–7A were based on the respective polymer emulsions of Examples 5–7. Each of the adhesive compositions included 100 pbw of a 55 wt % aqueous polymer emulsion, 15 pbw of a 55 wt % aqueous dispersion of epoxy resin (Daubond DC9010W55) and 1.2 pbw tetraethylenepentamine. The adhesive compositions of Examples 5A–7A each included KOH that, as noted above, had been added during synthesis of the polymers of Examples 5–7. The adhesive compositions of Examples 5A and 6A each included 0.16 wt % KOH and the adhesive composition of Example 7A included 0.33 wt % KOH. The adhesive compositions of Examples 5A–7A were tested according to the procedure set forth in Examples 1A–4A.

The results of the testing of the adhesive compositions of Examples 5A–7A are set forth below in Table 9.

TABLE 9

| Example # | Initial Bond Strength (g/in) | 24 Hour Bond Strength (g/in) | Bond Strength, 100% RH (g/in) |
|---|---|---|---|
| 5A | 177 | 450 | 227 |
| 6A | 227 | 686 | 370 |
| 7A | 132 | 510 | 254 |

EXAMPLES 8A AND 8B

The adhesive composition of Example 8A was of the same composition as the above-disclosed Example 6A. 5 parts by weight (pbw) of a 19.5 wt % aqueous solution of poly(vinyl alcohol) (Vinol V-205, Air Products) per 100 pbw polymer emulsion was added to the composition of Example 8A to form the adhesive composition of Example 8B. The compositions of Examples 8A and 8B were used to form laminates by the method disclosed above in Examples 1A–4A. The bond strength of the laminates was then tested by the method disclosed above in Examples 1A–4A, except that the strength of the bond formed was also measured using sample laminates that had been maintained at room temperature for 3 hours.

The amount of poly(vinyl alcohol), expressed as pbw per 100 pbw polymer emulsion (pVOH pbw per 100 pbw emulsion) and the results of the testing of the compositions of Examples 8A and 8B, including 3 Hour Bond Strength, expressed as grams/inch of peel (g/in) are set forth below in Table 10.

TABLE 10

| Example # | pVOH (pbw/100 pbw emulsion) | Initial Bond Strength (g/in) | 3 Hour Bond Strength (g/in) | 24 Hour Bond Strength (g/in) | Bond Strength, 100% RH (g/in) |
|---|---|---|---|---|---|
| 8A | 0 | 280 | 290 | 970 | 450 |
| 8B | 5 | 260 | 770 | ST | ST |

The results set forth in Table 10 indicate that the addition of the poly(vinyl alcohol) increase the rate of bond strength development and the ultimate bond strength of the adhesive composition of the present invention.

EXAMPLE 9A–9D

An adhesive composition the same as the above-disclosed Example 6 was used to make the laminates of Examples 9A–9D. A first substrate (a 0.00075 inch thick film of poly(ethyleneterephthalate)) was coated with about 1.5 pounds to 2 pounds of an adhesive composition per 3000 square feet coated substrate area on a forward gravure coater using a 130 quad gravure coating head at a coating speed of 250 feet per minute. The adhesive layer was dried at 200° F. to 210° F. The second substrate (a 0.0012 inch thick film of low density poly(ethylene)) was then bonded to the first substrate using a hot nip calendar roll at a nip temperature between 75° F. and 150° F.

The bond strength of the laminates was tested by the method disclosed above in Examples 1A–4A, except that the samples used in the humidity resistance testing were allowed to cure for 3 days under ambient conditions prior to placing the samples in the humidity chamber.

The nip temperatures, expressed as (Nip Temp (°F.)), used during bonding and the results of the testing of Examples 9A–9D a 3 Day Bond Strength expressed as grams/inch of peel (g/in).

TABLE 11

| Example # | Nip Temp (°F.) | Initial Bond Strength (g/in) | 24 Hour Bond Strength (g/in) | 3 Day Bond Strength (g/in) | Bond Strength 100% RH (g/in) |
|---|---|---|---|---|---|
| 9A | 140 | 360 | 950 | ST | ST |
| 9B | 120 | 250 | 820 | ST | ST |
| 9C | 100 | 250 | 910 | ST | ST |
| 9D | 77 | 200 | 730 | ST | ST |

The adhesive composition of the present invention provides improved initial bond strength, ultimate bond strength and humidity resistance. Laminates, particularly flexible polyolefin film laminates, wherein substrate layers are bonded together using the adhesive composition of the present invention are characterized by improved bond strength and improved resistance to humidity.

We claim:
1. An adhesive composition, comprising:
   from about 30 weight percent to about 70 weight percent solids dispersed in an aqueous medium, wherein the solids comprise:
   from about 60 weight percent to about 97.9 weight percent of a polymer having a glass transition temperature of about −40° C. to about 10° C., said polymer comprising first repeating units derived from an alkyl (meth)acrylate monomer, a vinyl ester monomer, a styrenic monomer or a mixture thereof, second repeating units derived from a hydroxyalkyl (meth)acrylate monomer, a monoethylenically unsaturated nitrogenous monomer or a mixture thereof;

from about 2 weight percent to about 30 weight percent of a polyfunctional epoxy resin, said polyfunctional epoxy resin including two or more epoxide groups per molecule;

from about 0.1 weight percent to about 10 weight percent of a polyfunctional curing agent, said polyfunctional curing agent including two or more functional groups, each selected from the group consisting of amino groups and amido groups, per molecule; and from about 0.01 weight percent to about 30 weight percent of a metal salt.

2. The composition of claim 1, wherein the first repeating units of the first polymer are each derived from a ($C_1$–$C_{20}$)alkyl (meth)acrylate monomer.

3. The composition of claim 1, wherein the second repeating units are each derived from a hydroxy($C_1$–$C_8$)alkyl (meth)acrylate monomer.

4. The composition of claim 1, wherein the epoxy resin is selected from the group consisting of reaction products of bisphenol A or bisphenol F and epichlorohydrin, epoxidized novolac resins, reaction products of epichlorohydrin and an aliphatic polyol, resins obtained by epoxidation with peracetic acid and mixtures thereof.

5. The composition of claim 1, wherein the curing agent is an aliphatic polyamine.

6. The composition of claim 1, wherein the polymer comprises no more than 1.0 wt % acid repeating units, said acid repeating units having at least one acid functional group per acid repeating unit, and wherein the composition includes from about 0.01 equivalent to about 2 equivalents of the metal salt per equivalent acid units of the polymer.

7. The composition of claim 6, wherein the polymer comprises less than or equal to about 0.5 weight percent acid repeating units derived from an monoethylenically unsaturated carboxylic acid monomer.

8. The composition of claim 7, wherein the monoethylenically unsaturated carboxylic acid monomer is acrylic acid, methacrylic acid or a mixture thereof.

9. The composition of claim 1, wherein the polymer further comprises from greater than 1.0 weight percent to about 11 weight percent acid repeating units, said acid repeating units having at least one acid functional group per acid repeating unit, and wherein the composition includes from about 0.01 equivalent to about 2 equivalents of the metal salt per equivalent of acid repeating units of the polymer.

10. The composition of claim 9, wherein the polymer comprises from about 0.5 weight percent to about 3 weight percent acid repeating units derived from an monoethylenically unsaturated carboxylic acid monomer.

11. The composition of claim 1, further comprising from about 0.1 part by weight to about 30 parts by weight of a water soluble hydroxy-functional polymer per 100 parts by weight polymer.

12. An adhesive composition, comprising from about 30 weight percent to about 70 weight percent solids dispersed in an aqueous medium, wherein the solids comprise:

from about 60 weight percent to about 97.9 weight percent of a polymer having a glass transition temperature of about −40° C. to about 10° C. and consisting essentially of first repeating units derived from an alkyl (meth)acrylate monomer, a vinyl ester monomer, a styrenic monomer or a mixture thereof, second repeating units derived from a hydroxyalkyl (meth)acrylate monomer, a monoethylenically unsaturated nitrogenous monomer or a mixture thereof, said polymer including no more than 1.0 weight percent acid repeating units, said acid repeating units having at least one acid functional group per acid repeating unit;

from about 2 weight percent to about 30 weight percent of a polyfunctional epoxy resin, said polyfunctional epoxy resin including two or more epoxide groups per molecule; and from about 0.1 weight percent to about 10 weight percent of a polyfunctional curing agent, said polyfunctional curing agent including two or more functional groups, each selected from the group consisting of amino groups and amido groups, per molecule.

13. The composition of claim 12, wherein the polymer includes less than or equal to about 0.5 weight percent acid repeating units derived from a monoethylenically unsaturated carboxylic acid monomer.

14. The composition of claim 13, wherein the polymer consists essentially of from about 85 wt % to about 95 wt % first repeating units derived from an alkyl (meth)acrylate monomer, a vinyl ester monomer, a styrenic monomer or a mixture thereof and from about 5 wt % to about 15 wt % second repeating units derived from a hydroxyalkyl (meth)acrylate monomer.

15. The composition of claim 12, further comprising from about 0.1 part by weight to about 30 parts by weight of a water soluble hydroxy-functional polymer per 100 parts by weight polymer.

16. A laminate, comprising a first substrate layer, a second substrate layer and an adhesive layer interposed between the first and second substrate layers and bonding the first and second substrate layers together, wherein the adhesive layer comprises the solids of the adhesive composition of claim 1.

17. The laminate of claim 16, wherein at least one of the substrate layers is a polyolefin film.

18. A laminate, comprising a first substrate layer, a second substrate layer and an adhesive layer interposed between the first and second substrate layers and bonding the first and second substrate layers together, wherein the adhesive layer comprises the solids of the adhesive composition of claim 11.

19. The laminate of claim 18, wherein at least one of the substrate layers is a polyolefin film.

20. A method for making a laminate, comprising:

applying a layer of the composition of claim 1 to a first substrate layer; and contacting the layer of adhesive composition with a second substrate layer to form the laminated article.

21. A laminate made by the process of claim 20.

22. A method for making a laminate, comprising:

applying a layer of the composition of claim 12 to a first substrate layer; and contacting the layer of adhesive composition with a second substrate layer to form the laminated article.

23. A laminate made by the process of claim 22.

24. The composition of claim 12, wherein the polymer includes less than or equal to about 0.8 weight percent acid repeating units derived from a monoethylenically unsaturated carboxylic acid monomer.

* * * * *